United States Patent
Torp et al.

(10) Patent No.: US 11,272,901 B2
(45) Date of Patent: Mar. 15, 2022

(54) ULTRASOUND BLOOD-FLOW MONITORING

(71) Applicant: Cimon Medical AS, Trondheim (NO)

(72) Inventors: Hans Torp, Trondheim (NO); Torbjorn Hergum, Os (NO)

(73) Assignee: Cimon Medical AS, Trondheim (NO)

( * ) Notice: Subject to any disclaimer, the term of this patent is extended or adjusted under 35 U.S.C. 154(b) by 346 days.

(21) Appl. No.: 16/323,174

(22) PCT Filed: Aug. 4, 2017

(86) PCT No.: PCT/GB2017/052309
§ 371 (c)(1),
(2) Date: Feb. 4, 2019

(87) PCT Pub. No.: WO2018/025050
PCT Pub. Date: Feb. 8, 2018

(65) Prior Publication Data
US 2019/0175138 A1 Jun. 13, 2019

(30) Foreign Application Priority Data
Aug. 5, 2016 (GB) ...................... 1613530

(51) Int. Cl.
*A61B 8/06* (2006.01)
*A61B 8/00* (2006.01)
*A61B 8/08* (2006.01)

(52) U.S. Cl.
CPC .............. *A61B 8/06* (2013.01); *A61B 8/4227* (2013.01); *A61B 8/4236* (2013.01);
(Continued)

(58) Field of Classification Search
CPC ......... A61B 8/54; A61B 8/5223; A61B 8/488; A61B 8/4483; A61B 8/4236; A61B 8/4227; A61B 8/0891; A61B 8/06
See application file for complete search history.

(56) References Cited

U.S. PATENT DOCUMENTS 3,554,030 A   1/1971 Peronneau
4,067,236 A   1/1978 Hottinger
(Continued)

FOREIGN PATENT DOCUMENTS

CN   1189217   7/1998
CN   102440002   5/2012
(Continued)

OTHER PUBLICATIONS

Atkinson et al., "Pulse-Doppler Ultrasound and Its Clinical Application", The Yale Journal of Biology and Medicine, vol. 50, pp. 367-373, 1977.
(Continued)

*Primary Examiner* — Boniface Ngathi
(74) *Attorney, Agent, or Firm* — Diedericks & Whitelaw, PLC.

(57) ABSTRACT

A system for monitoring blood flow in a patient comprises a first unit having an ultrasound transducer and a fastener for fastening the unit to the patient. A controller subsystem comprises the first unit and a separate second unit. The controller subsystem is configured to: control the ultrasound transducer to transmit plane-wave pulses into the patient in a propagation direction; sample reflections of the plane-wave pulses, received at the ultrasound transducer, from a region within the patient, to generate pulse-Doppler response signals; and process the pulse-Doppler response signals to estimate a series of values, over time, of a measure proportional, but not equal, to the total blood volume flow passing through the region. A monitoring subsystem is configured to monitor the series of values over time and to generate a signal if a set of one or more of the values satisfies a predetermined criterion.

20 Claims, 4 Drawing Sheets

(52) U.S. Cl.
CPC ............ *A61B 8/4483* (2013.01); *A61B 8/488* (2013.01); *A61B 8/5223* (2013.01); *A61B 8/54* (2013.01); *A61B 8/0891* (2013.01)

(56) References Cited

U.S. PATENT DOCUMENTS

| | | | |
|---|---|---|---|
| 4,509,526 | A | 4/1985 | Barnes et al. |
| 4,757,823 | A | 7/1988 | Hofmeister et al. |
| 4,993,417 | A | 2/1991 | Seo |
| 5,152,293 | A | 10/1992 | Vonesh et al. |
| 5,284,147 | A | 2/1994 | Hanaoka et al. |
| 5,560,363 | A * | 10/1996 | Torp .................... A61B 8/06 600/455 |
| 6,176,143 | B1 | 1/2001 | Mo et al. |
| 6,666,357 | B2 | 12/2003 | Bougamont et al. |
| 6,746,402 | B2 | 6/2004 | Ustuner |
| 7,413,545 | B2 | 8/2008 | Muramatsu et al. |
| 9,597,055 | B2 | 3/2017 | Kabakov et al. |
| 2003/0013947 | A1 | 1/2003 | Frattarola |
| 2006/0111633 | A1 | 5/2006 | McMorrow |
| 2009/0048512 | A1 | 2/2009 | Maeva et al. |
| 2009/0105594 | A1 | 4/2009 | Reynolds et al. |
| 2010/0210947 | A1 | 8/2010 | Burcher et al. |
| 2015/0374540 | A1 | 12/2015 | Lopath et al. |
| 2016/0278736 | A1 | 9/2016 | Hamilton et al. |

FOREIGN PATENT DOCUMENTS

| | | |
|---|---|---|
| CN | 103284753 | 9/2013 |
| CN | 104706382 | 6/2015 |
| CN | 107296628 | 10/2017 |
| EP | 0014793 | 9/1980 |
| EP | 2303131 | 4/2011 |
| EP | 2918232 | 9/2015 |
| EP | 2940487 | 11/2015 |
| GB | 2047404 | 11/1980 |
| JP | 10328189 | 12/1996 |
| JP | 2015150366 | 8/2015 |
| WO | 9208408 | 5/1992 |
| WO | 9502361 | 1/1995 |
| WO | 2009158399 | 12/2009 |
| WO | 2013014647 | 1/2013 |
| WO | 2013154229 | 10/2013 |
| WO | 2014107769 | 7/2014 |
| WO | 2017109080 | 6/2017 |
| WO | WO-2017096487 A1 * | 6/2017 ............... A61B 8/06 |

OTHER PUBLICATIONS

Flochec Digital ABI System, "Semler Scientific, Inc." pp. 1-2, 2013.
Kasai et al., "Real-Time Two-Dimensional Blood Flow Imaging Using an Autocorrelation Technique", IEE Transactions on Sonics and Ultrasonics, vol. SU-32, No. 3, pp. 458-464, 1985.
Laerdal "Movo Fetal Heart Rate Monitor User Guide" pp. 1-56, 2015.
Obrien Jr., "Single-Element Transducers" AAPM Tutorial Radio Graphis, vol. 13, No. 4, pp. 947-957, 1993.
Spectromed JSC "Sonomed-300M Transcranial Doppler System User's Manual" 2011.
Stugaard et al., "Abnormalities of left ventricular filling in patients with coronary artery disease: assessment by colour M-mode Doppler technique" vol. 15, No. 3, pp. 318-327, 1994.
Torp et al., "Doppler Ultrasound" Comprehensive Biomedical Physics, pp. 343-360, 2014.

* cited by examiner

ULTRASOUND BLOOD-FLOW MONITORING

CROSS-REFERENCE TO RELATED APPLICATIONS

This application represents the U.S. National Phase of International Application number PCT/GB2017/052309 entitled "Ultrasound Blood-Flow Monitoring" filed 4 Aug. 2017, which claims priority from and the benefit of United Kingdom patent application No. 1613530.3, filed 5 Aug. 2016, all of which are incorporated herein by reference.

BACKGROUND OF THE INVENTION

This invention relates to monitoring blood flow in an organism using ultrasound.

There are many clinical situations in which is helpful to monitor peripheral blood flow in a human or animal patient. For example, it can be important to monitor the flow of blood in the brain of a baby that has been born prematurely, so that treatment can be started quickly in case reduced blood flow is detected. It can also be useful to monitor the microcirculation of a patient in the hours following vascular surgery in order to detect occlusions of peripheral bypasses.

Various techniques have been used to analyse blood flow. These include laser Doppler scanning, near-infrared spectroscopy, and Doppler ultrasound imaging. However, such analyses must typically be performed by a skilled technician, who must be present with the patient throughout. The equipment for carrying out such analyses can also be very expensive (e.g., over one million U.S. dollars for a 3D ultrasound imaging system). Such techniques are therefore not well suited to the unattended monitoring of patients in hospital wards.

The present invention seeks to provide a better approach.

SUMMARY OF THE INVENTION

From a first aspect, the invention provides a system for monitoring blood flow in an organism, the system comprising:
- an ultrasound transducer; and
- a controller subsystem configured to:
  (i) control the ultrasound transducer to transmit plane-wave pulses into the organism in a propagation direction;
  (ii) sample reflections of the plane-wave pulses, received at the ultrasound transducer, from a region within the organism, to generate pulse-Doppler response signals; and
  (iii) process the pulse-Doppler response signals to estimate a series of values, over time, of a measure proportional to the total blood volume flow passing through the region.

From a second aspect, the invention provides a method of monitoring blood flow in an organism, the method comprising:
- transmitting plane-wave pulses into the organism in a propagation direction;
- sampling reflections of the plane-wave pulses from a region within the organism, to generate pulse-Doppler response signals; and
- processing the pulse-Doppler response signals to estimate a series of values, over time, of a measure proportional to the total blood volume flow passing through the region.

Thus it will be seen by those skilled in the art that, in accordance with the invention, a low-cost, unfocused ultrasound transducer can be used to monitor blood flow, qualitatively, through a region in an organism. This contrasts with prior-art approaches that attempt to calculate an absolute measure of blood flow in a single blood vessel. In other words, in embodiments of the present invention, the measure is proportional to, but not equal to, the total blood volume flow. Such prior-art approaches typically require expensive transducers, complex processing systems, and a skilled operator. Instead, the present inventor has realised that values of a relative measure of blood volume flow within a region can be obtained at much lower cost, and without the need for a skilled operator, and yet still provide clinically-important information about the organism. The inventor has further realised that it is possible to obtain such values without requiring an imaging system, because the measure can be made independent of the angle of the transducer relative to the blood vessels in the region (as is explained in more detail below).

While the invention could be practised using an array-based ultrasound transducer, in a preferred set of embodiments the ultrasound transducer is a single-element transducer. The element may be a piezoelectric element. The same element in the ultrasound transducer preferably both transmits and receives ultrasound. This enables the cost of the transducer to be kept low. The transducer preferably emits ultrasound from a planar face. The planar face preferably has a width (e.g., a maximum, minimum or mean width) that is large compared with that of traditional focused ultrasound transducers—for example, having a width of at least 2 mm, 5 mm, 10 mm, 20 mm or more. The transducer preferably transmits ultrasound energy in a substantially uniform beam—i.e., having a constant cross-section in the propagation (depth) direction. The transducer (or a transmitting face thereof) may have any shape, but in one set of embodiments it is circular. It may therefore transmit a cylindrical beam into the organism—e.g., having a diameter of 10 mm. By not focusing the beam, the intensity of the plane-wave transmissions is substantially uniform across the region; this allows the measure proportional to the total blood volume flow to be estimated (or calculated, within the precision limits of the system and any noise or other sources of error). This would not typically be possible with a focused beam, the intensity of which would vary across the region, and across individual blood vessels. Prior-art ultrasound blood-flow imaging systems, which use focused beams, can therefore only measure blood velocity, rather than total volume flow.

A lateral extent of the region within the organism is preferably determined by the shape of the transducer (or a transmitting face thereof). An axial extent of the region (i.e., in the propagation direction, also referred to herein as the depth direction) may be determined by the duration of each pulse and by a time delay at which the reflections are sampled, after the transmission of each pulse. Range gating may be used to control the axial extent of the region. In some embodiments, the region has a depth of between 0.15 mm to 1 mm.

The present invention is particularly well suited to determining blood flow close to the transducer. This is because a broad, unfocused beam means that the reflection from each blood cell is relatively weak. The region may therefore have a maximum distance from the transducer, in the propagation direction, that is less than a width (e.g., a maximum, minimum or mean width) of the transducer, or that is no more than two, three, five or ten times this width.

In some embodiments, reflections of the plane-wave pulses are sampled from each of a plurality of regions within the organism—preferably at a plurality of different distances from the transducer—e.g., from a plurality of pairwise abutting or overlapping regions. The regions may all have the same thickness, which may be between 0.15 mm to 1 mm. The furthest region from the transducer is preferably still at a maximum distance from the transducer, in the propagation direction, that is less than a width (e.g., a maximum, minimum or mean width) of the transducer, or that is no more than two, three, five or ten times this width. Respective series of values of the measure proportional to the total blood flow through the respective region may be determined for each of the regions.

The plane-wave pulses are preferably transmitted at intervals—preferably at regular intervals. A pulse repetition frequency of around 10 kHz may be used. The transmitted pulses are preferably sine-wave pulses having a common carrier frequency. A pulse-Doppler response signal could possibly be generated from the reflections of just one pulse. However, in order to provide useful depth resolution, each pulse needs to be brief, and will therefore typically be too short to allow Doppler frequency shifts to be measured from the reflection of just a single pulse. (The bandwidth of a single pulse might typically be around 1 MHz, whereas the Doppler shift from a blood cell in the region could be around 1 kHz.) Therefore, each value of the measure proportional to the total blood volume flow through the region is preferably determined from the reflections of a plurality of pulses (for example, around fifty pulses). A sample may be obtained from each of a plurality of pulses, and this plurality of samples may then be used to generate a pulse-Doppler response signal, which may be processed to estimate a value of the measure.

In some embodiments, the pulse-Doppler response signals are complex-demodulated. The response signals are preferably shifted to baseband. In some embodiments, a Hilbert transform may be applied to the pulse-Doppler response signals. The response signals may be filtered—e.g., to reduce thermal noise.

Although the pulses are described herein as a plane-wave pulses, the skilled person will appreciate that, in practice, the wavefront may not be exactly planar—e.g., due to imperfections in the transducer, or due to interference (e.g., refraction and diffraction) as the waves travel, or due to the finite extent of the wavefront. The pulses are preferably unfocused. The transducer preferably has no acoustical lens. The propagation direction may change over time—e.g., due to intentional or accidental movement of the transducer relative to the organism.

The series of values of the measure proportional to the total blood volume flow through the region may comprise two, three, ten or more values. Each value preferably relates to blood flow through the region at a different point in time. These points in time may span an interval longer than a minute, or longer than 30, 60, 120 or 240 minutes or more. The series of values may be monitored by a monitoring subsystem. A signal may be generated if a set of one or more of the values satisfies a predetermined criterion, such as if a value drops below a threshold amount (which may be determined relative to one or more earlier values), or if the series of values drops faster than a threshold rate. The signal may cause an alarm to be raised—e.g., by sounding an audible alert or by sending a message over a network connection. The system may be a patient monitoring system—e.g., for bedside use in hospital. The series of values may be monitored for a period of time longer than a minute, or longer than 30, 60, 120 or 240 minutes or more.

The pulse-Doppler response signals may be processed in any suitable way to estimate the values of the measure proportional to the total blood flow through the region. The relationship of the measure to the total blood volume flow through the region (i.e., the coefficient of proportionality) is preferably fixed for the series of values.

The sampled reflections may be processed to remove noise, or in other ways, when generating the response signals. For example, to remove or attenuate thermal noise, the controller subsystem may be configured to estimate a power spectrum relating to thermal noise—e.g., generated from signals received when the ultrasound transducer is inactive (i.e., containing no reflections)—and may be configured to subtract the power spectrum of the thermal noise from a power spectrum generated from the sampled reflections. Because thermal noise should be constant for all frequencies, it may be sufficient to estimate the power of the thermal noise and subtract this from a power spectrum generated from the sampled reflections equally across the frequency spectrum.

In a preferred set of embodiments, each value of the measure is determined from a respective power-weighted mean frequency (or, more generally, a power-weighted average frequency, for any suitable definition of an average) of at least part of one of the pulse-Doppler response signals. The blood-flow measure may equal the power-weighted mean frequency, or it may be a function of the power-weighted mean frequency. The controller subsystem is preferably arranged to calculate a power-weighted mean frequency from a response signal. This mean value may be calculated over the whole of a pulse-Doppler response signal, or over part of the response signal (e.g., over a particular range of frequencies). A value representing a power-weighted mean frequency may be stored in a memory—e.g., in RAM or in a register of the system—as part of the processing (this value may be the mean frequency, or it may be a suitable representative value, such as rounded value of the mean frequency, or a mathematically-equivalent representation of the mean frequency). A respective power-weighted mean frequency value may be calculated from reflections of a respective series of plane-wave pulses—e.g., every fifty or so pulses.

The power-weighting may be applied in any appropriate way—e.g., by multiplying each of a set of frequency values or bins by a measure of the power or amplitude of the pulse-Doppler response signal at or in that frequency value or bin. In some embodiments, a power-weighted mean frequency may be calculated as an integral. In other embodiments, it may be calculated using autocorrelation.

In some embodiments, the controller subsystem is configured to integrate, over a set of frequencies, a function of the power spectrum of one of the pulse-Doppler response signals (preferably shifted to baseband). The function may be power multiplied by frequency. The power spectrum may be determined using a Fourier analysis—e.g., by taking a fast Fourier transform of the pulse-Doppler response signal, after complex demodulation. The function of the power spectrum may be integrated over any suitable set of frequencies. In some embodiments, it may be integrated over all frequencies in a Fourier transform. However, in other embodiments, the set of frequencies may exclude frequencies in a band around zero (corresponding to frequencies close to the carrier frequency of the transmitted pulses before demodulation). This may be achieved by applying a high-pass filter (e.g., with a cut-off frequency of between around 50 Hz to around 500 Hz) to the pulse Doppler response signal, shifted to baseband. In this way, reflections from stationary or slow-moving "clutter" can be filtered out, so that only reflections from faster-moving tissues, such as blood, are included in the integral. Contributions from slow-moving blood may be excluded by such a high-pass filter; however, the contribution of such slow-moving blood to the total blood volume flow through the region will typically be small and may therefore be regarded as negligible.

The set of frequencies over which the function of the power spectrum is integrated may include only positive frequencies (corresponding to frequencies higher than those of the transmitted pulses before demodulation), so that only flow in a direction having a component towards the transducer is included. Alternatively, the set of frequencies may include only negative frequencies (corresponding to frequencies lower than those of the transmitted pulses before demodulation), so that only flow in a direction having a component away from the transducer is included. The system may be configured to receive an input to selectively limit the processing to only positive frequencies or to only negative frequencies. In this way, a physician can choose to monitor flow in just one direction, which may be useful if, for example, one particular major artery is of interest in a region.

In some embodiments, the controller subsystem is configured to calculate a power-weighted mean frequency from a pulse-Doppler response signal using autocorrelation. The controller may be configured to calculate the power-weighted mean frequency using an autocorrelation function of the complex envelope signal of part or all of the response signal. The controller may comprise one or more conjugate complex multipliers for carrying out the autocorrelation. The autocorrelation function may be determined using a lag of one sample. The power-weighted mean frequency may be calculated by multiplying the signal power of the response signal with the complex autocorrelation function.

The factor by which the measure is proportional to the total blood volume flow (coefficient of proportionality) is typically not known, as it will depend on the scattering co-efficient of the blood, as well as attenuation of the ultrasound wave between the transducer and the blood vessel. However, it may be assumed to be constant over the series of values, allowing for a meaningful analysis of the series of values.

In some situations, an assumption that the attenuation is constant may not be justified—for example, if a probe containing the ultrasound transducer is moving (even slightly) relative to the organism. Thus, in some embodiments, the processing of the pulse-Doppler response signals comprises compensating for attenuation between the transducer and the region. This may be done by scaling the measure proportional to the total blood volume flow through the region according to an estimate of the attenuation. The estimate of attenuation may be updated at intervals, to allow for dynamic relative movement of the transducer. In some embodiments, the controller subsystem is configured to apply a low-pass filter to a baseband-shifted pulse-Doppler response signal, and to divide an estimate of the measure by the signal power after the low-pass filter. The low-pass filter may be set to pass signals from stationary and slower-moving tissue surrounding blood vessels (muscles, vessel walls, etc.) but to filter out signals from the faster-moving blood. The filter may have a cut-off frequency of between around 50 Hz to around 500 Hz. (This is equivalent to filtering signals in a band around the frequency of the transmitted plane-wave pulses, if no complex demodulation is performed). The low-pass filter may be the complement to the clutter filter described above. Because the attenuation will typically affect high-frequency and low-frequency reflections by the same amount, dividing the measure by the low-frequency signal power should remove the effect of the attenuation.

In some embodiments, one value of the measure may be estimated every 5 milliseconds, or every 10 milliseconds, or somewhere in between. A blood flow curve may be calculated from a series of values, which may be generated from partially-overlapping time periods. This blood flow curve preferably has sufficient time resolution for wave form analysis. The controller may be configured to calculate, from the blood flow curve, a time average over a plurality of heartbeats. The controller may be configured to calculate a pulsative index and/or a resistive index from the blood flow curve. These indices are related to the elastic property of blood vessels in the region.

A plurality of series of values of the measure may be determined with different peripheral resistances. These may be used to estimate a parameter proportional to volume compliance—e.g., by combining the waveform with a Wind Kessel-model.

Data representing any of: the series of values proportional to the total blood volume flow in a region, a blood flow curve, a pulsative index, a resistive index, a parameter proportional to volume compliance, and any other intermediate value or output value, may be stored in a memory of the system, or may be output over a data connection, or may be displayed on a screen.

The blood-flow monitoring system, and its controller subsystem, may comprise one or more processors, DSPs, ASICs, volatile memory, non-volatile memory, inputs, outputs, etc. as will be appreciated by one skilled in the art. Some or all of the operations described herein may be carried out by, or under the control of, software stored in a memory and executing on one or more processors in the controller or monitoring system. The monitoring system may be a single unit or it may be distributed—e.g. with one or more operations being performed remotely from the living organism, such as on a remote server. A sampling module in the controller subsystem may comprise an amplifier and/or a ADC and/or one or more filters and/or demodulators.

In particular the controller subsystem may comprise two separate units—i.e. a first unit and a second unit. The first unit may control the transducer and sample the reflections. The second unit may estimate the series of values from the pulse-Doppler response signals. The first unit or the second unit may sample the reflections of the plane-wave pulses. The two units may communicate over a wired link, such as a USB cable, or a wireless link, such as a Bluetooth™ connection. In particular, the first unit may send data representing the pulse-Doppler response signals (preferably after bandpass filtering and complex demodulation) to the second unit, preferably wirelessly. The first unit may comprise a power supply, such as a battery. The first unit may comprise the ultrasound transducer, e.g., within a common housing-preferably a solid housing such as a box. The first unit may comprise means for fastening the first unit to a patient, such as a strap or an adhesive pad or region, or any other suitable fastener. The second unit may comprise a display. The second unit may be a mobile telephone (cell phone) or a tablet computer or other portable device. By dividing the system in this way, the first unit can be a portable sensor unit, which can easily be attached to a patient without the inconvenience of wired leads, and can be relatively low-cost, because it need only comprise a relatively basic microcontroller, while the more-complex processing of the response signals can be carried out on a more powerful device.

The operations described herein need not necessarily be performed close in time to one another. In particular, the reflected ultrasound signals may be acquired at a first period in time, and then processed at a later period of time, which may be days apart.

The present system has many applications—e.g., neonatal monitoring, post-operative care, monitoring cerebral circulation, monitoring microcirculation, monitoring for sudden blood loss in an emergency setting, etc.

The inventor has realised that the same principle may be applied in settings other than just blood and thus, from a further aspect, the invention provides a system for monitoring fluid flow, the system comprising:
an acoustic transducer;
a controller configured to:
(i) control the acoustic transducer to transmit plane-wave pulses in a propagation direction;
(ii) sample reflections of the plane-wave pulses, received at the acoustic transducer, from a region, to generate pulse-Doppler response signals; and
(iii) process the pulse-Doppler response signals to estimate a series of values, over time, of a measure proportional to the total fluid volume flow through the region.

From another aspect, the invention provides a method of monitoring fluid flow, the method comprising:
transmitting plane-wave acoustic pulses in a propagation direction;
sampling reflections of the plane-wave pulses from a region, to generate pulse-Doppler response signals; and
processing the pulse-Doppler response signals to estimate a series of values, over time, of a measure proportional to the total fluid volume flow through the region.

The fluid could be any liquid or gas. The acoustic pulses may be ultrasound pulses. Any of the optional features described above may be features of these aspects also.

Features of any aspect or embodiment described herein may, wherever appropriate, be applied to any other aspect or embodiment described herein. Where reference is made to different embodiments or sets of embodiments, it should be understood that these are not necessarily distinct but may overlap.

BRIEF DESCRIPTION OF THE DRAWINGS

Certain preferred embodiments of the invention will now be described, by way of example only, with reference to the accompanying drawings, in which.

DETAILED DESCRIPTION OF THE PREFERRED EMBODIMENTS

Figure 1:
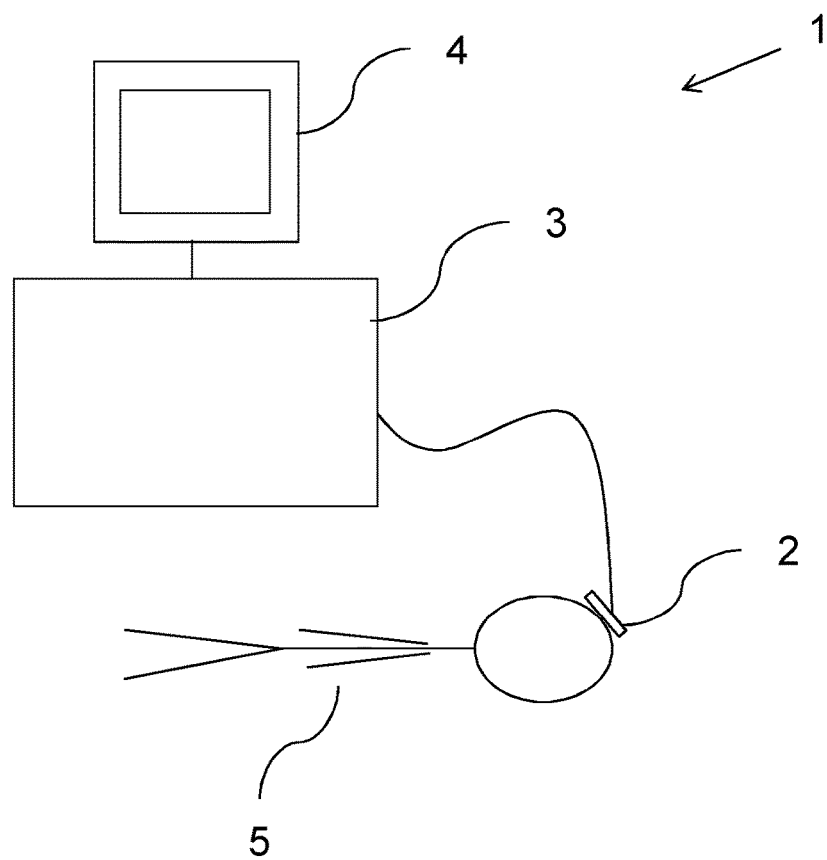
FIG. 1 is a diagram of a scanning system embodying the invention.

FIG. 1 shows an ultrasound-based blood-flow monitoring system 1. It includes a piezoelectric ultrasound transducer 2, a processing unit 3, and a display device 4. The ultrasound transducer 2 has a single, flat, circular active element, of approximately 10 mm diameter, contained in a suitable housing. It is connected to the processing unit 3 by a wire. The processing unit 3 is connected to the display device 4.

The transducer 2 can transmit ultrasonic plane waves (e.g., as a series of pulses) and can also receive reflections of the waves, under the control of the processing unit 3. The transducer 2 may be arranged to be fastened to a patient 5 such as a premature infant—e.g., by one or more straps, or adhesive pads.

The transducer 2 can be fastened to a patient 5 by a clinician or technician and then left unattended for the monitoring system 1 to monitor microcirculatory blood flow. The monitoring system 1 may output data such as a real-time plot of a blood flow curve on the display 4. It may also signal an alert if a predetermined criterion is met, such as if the blood flow drops rapidly. The alert may show on the display 4, or audibly, or be sent to another device over a network connection.

The system 1 may be used to monitor cerebral circulation in a premature baby, or to monitor peripheral circulation after an operation, or for many other situations where changes in blood flow can provide a useful indication of the status of the patient 5.

Figure 2:
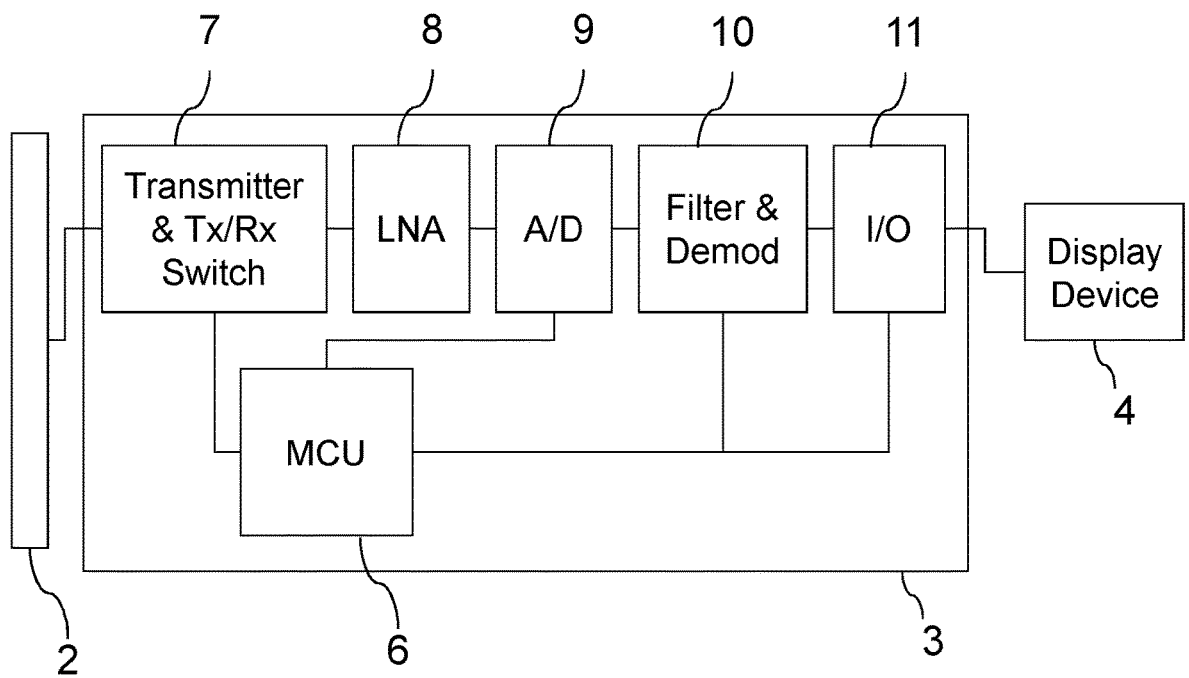
FIG. 2 is a schematic drawing of functional elements of the scanning system.

FIG. 2 shows more details of the system 1. The processing unit 3 contains a microcontroller (MCU) 6. Alternatively, this could be one or more CPUs, DSPs, or other processing means. A combined transmitter and transmit/receive switch unit 7 in the processing unit 3 is connected to the transducer 2. It can cause the transducer 2 to transmit plane wave pulses (e.g., 10 microseconds long) at a predetermined carrier frequency (e.g., 2 MHz) and at a predetermined repetition rate (e.g., 10 kHz). This transmitter unit 7 can switch between a transmitting mode and a receiving mode at the repetition rate (e.g., 10 kHz), under control of the microcontroller 6, in order to receive echoes from each pulse at the transducer 2. The transmitter unit 7 outputs received reflections to a low-noise amplifier (LNA) 8 in the processing unit 3, which amplifies the received reflection signals. The LNA 8 outputs to an analogue-digital converter (A/D) 9 in the processing unit 3, which samples and digitises the received reflections from each pulse.

The sampled reflections (pulse-Doppler response signals) are then bandpass filtered and demodulated in a filter and complex demodulator unit 10 in the processing unit 3. The demodulated pulse-Doppler response signals may be sent to the microcontroller 6 for further processing. The microcontroller 6 may calculate estimates of blood volume flow, and send data related to the blood flow to the display device 4 (which may be separate from the processing unit 3, or may be integral to it), via an input/output (I/O) unit 11, for displaying to a user.

Alternatively, the demodulated pulse-Doppler response signals may be passed directly to the external display device 4 (which could be a mobile telephone or tablet computer) via the input/output (I/O) unit 11, and the display device 4 may calculate the estimates of blood volume flow from the response signals. In this case, the I/O unit 11 may be a wireless-communication unit, such as a Bluetooth™ radio.

In an alternative embodiment, the ultrasound transducer 2 may be integrated with the processing unit 3 in a common housing, rather than being connected by a wire. The processing unit 3 is then preferably very compact. It may be battery powered. The I/O unit 11 is preferably wireless (e.g., a Bluetooth™ radio). In this way, the combined processing unit 3 and transducer 2 form a highly portable sensor unit. The sensor unit preferably transmits demodulated signals to a separate display device 4, for processing; this allows the processing unit 3 to have a relatively basic microprocessor 6, allowing it to be made at low cost.

The microcontroller 6 and/or display device 4 processes the demodulated response signals to obtain a series of estimates of blood volume flow within the patient 5 using one of the techniques described below.

Figure 3:
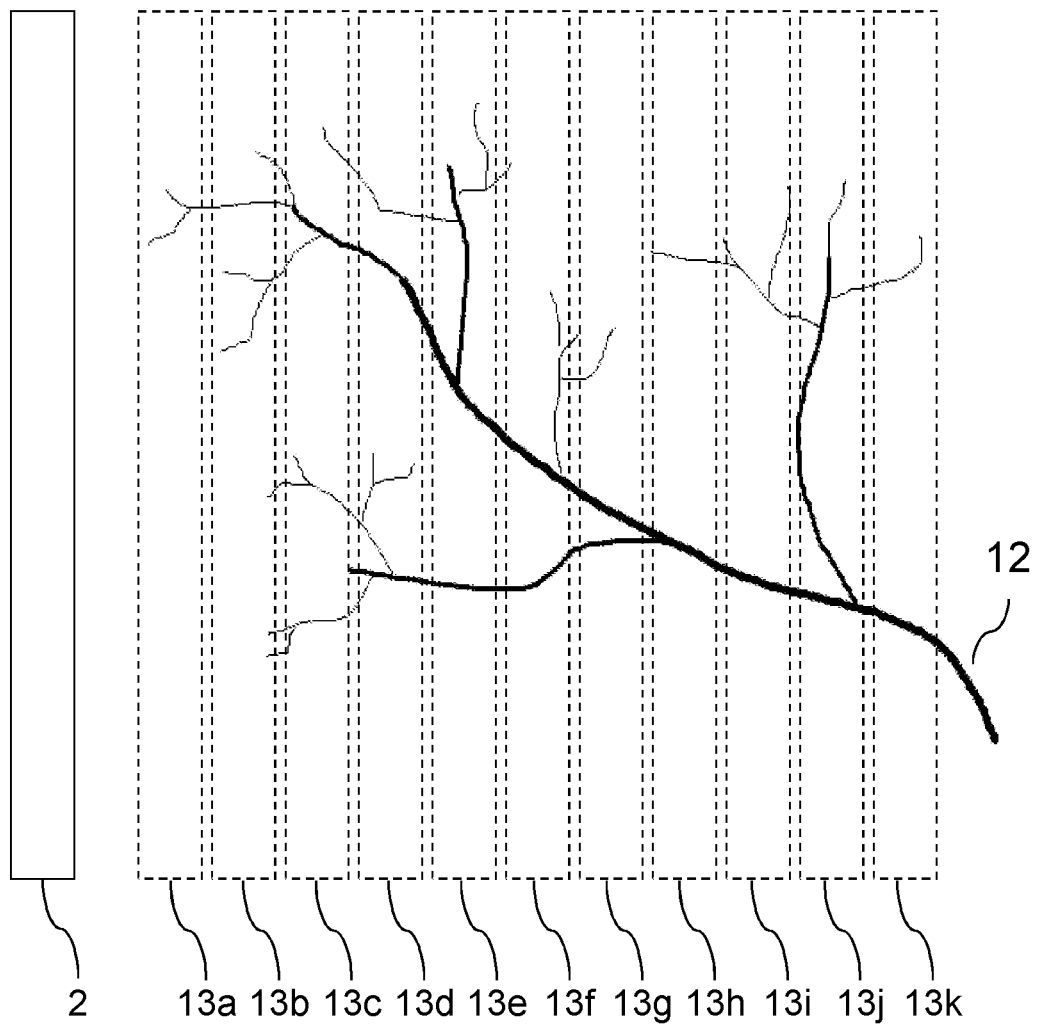
FIG. 3 is a simplified cross-section through a blood supply system and an ultrasound transducer.

FIG. 3 shows a branching blood vessel system 12 in cross section. The blood vessel system 12 may be a few millimetres or a centimetre or two below the surface of the skin of the patient 5. The ultrasound transducer 2 at the left side of FIG. 3 is attached to the patient 5. It transmits plane waves into the patient 5 in a cylindrical beam. The axis of the cylinder runs from left to right in FIG. 3. Returning reflections are sampled after each pulse. One sample is obtained for each of a set of cylindrical sample volumes 13a-13k in the patient 5, with the delay after the transmission of the pulse determining how far each sample volume 13a-13k is from the face of the transducer 2.

The transducer 2 is an unfocused, disc shaped transducer, without acoustical lens, which has considerably larger dimensions than prior-art focused transducers or array transducers—e.g. a circular disc with diameter 10 mm. This will generate a uniform beam with constant cross section in the depth direction—e.g. a cylindrical beam with diameter 10 mm. The spatial sensitivity in receive will also be constant within the beam width, so that the cross-sectional area of the sample volume will be much larger, compared with a focused beam. This means that the system 1 will capture blood flow signals from a much larger area than a focused transducer could, and the probe location and orientation becomes less critical. A drawback with the broad beam compared to the focused beam, is that the signal from each individual blood cell becomes weaker. This introduces a limitation in the maximum depth that can be measured. The technique is therefore not applicable to deep vessels.

Samples from a series of pulses (e.g. 50 pulses) are collected for each volume 13a-13k, and are filtered and complex demodulated by the demodulator unit 10 to give a respective baseband pulse-Doppler response signal for each volume 13a-13k every 5 milliseconds.

By using a multi-gated Doppler technique, the signal is split into a large number of Doppler signals, each representing blood flow through a thin "slice" or volume 13a-13k perpendicular to the ultrasound beam. The thickness d of the slices is given by the length of the transmitted pulse: $d=N*\lambda/2$, where N is the number of periods in the transmitted pulse and $\lambda$ is the ultrasound beam wavelength. Typical values for the thickness d are 0.15 mm to 1 mm (e.g., 0.5 mm). By frequency analysis of the Doppler signal from each volume 13a-13k (for example, by fast Fourier transform), a Doppler frequency spectrum is obtained, where the power density of each frequency component is given by the number of blood cells with a specific velocity component perpendicular to the transducer 2.

For each volume 13a-13k, the blood flow value will measure the amount of blood flow for all the blood vessels that pass that volume, and will provide a measure that is independent of the angle between the ultrasound beam and the blood vessels. This is illustrated in FIGS. 4, 5 and 6.

Figure 4:
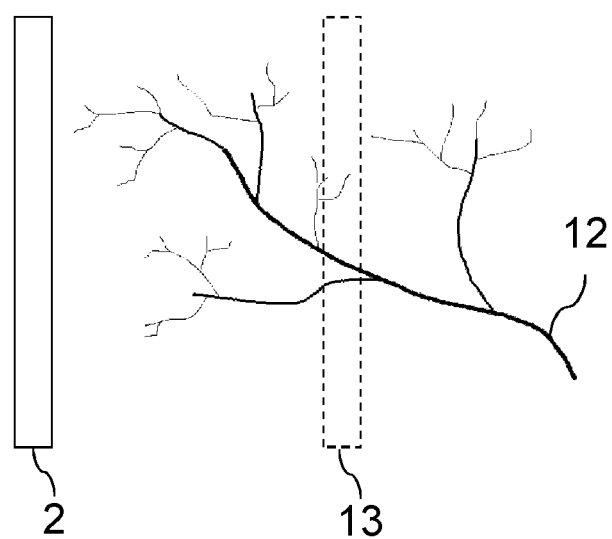
FIG. 4 is a simplified cross-section with the ultrasound transducer in a first orientation.

FIG. 4 shows the transducer 2 in a first orientation, with an exemplary volume 13 intersecting the blood vessel system 12.

Figure 5:
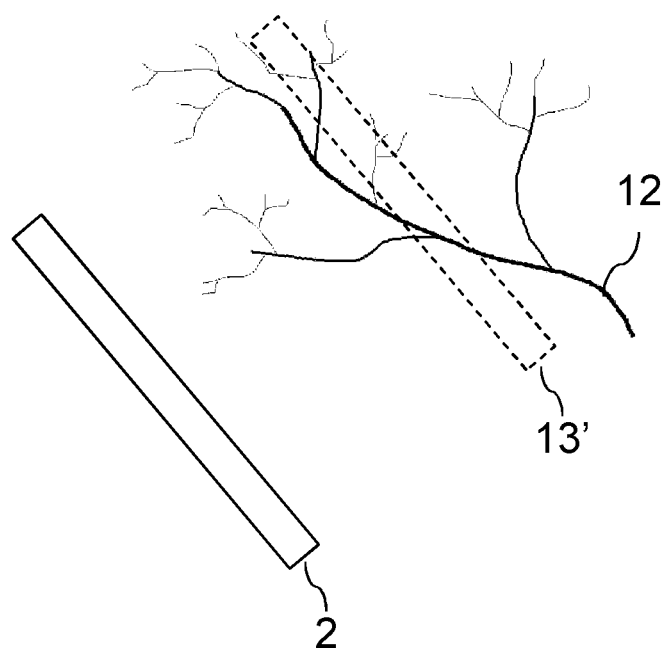
FIG. 5 is a simplified cross-section with the ultrasound transducer in a second orientation.

FIG. 5 shows the transducer 2 in a second orientation, with a different exemplary volume 13' intersecting the blood vessel system 12 at a different angle. The same major vessels (which account for the majority of the blood flow) are intersected in the first and second orientations.

Figure 6:
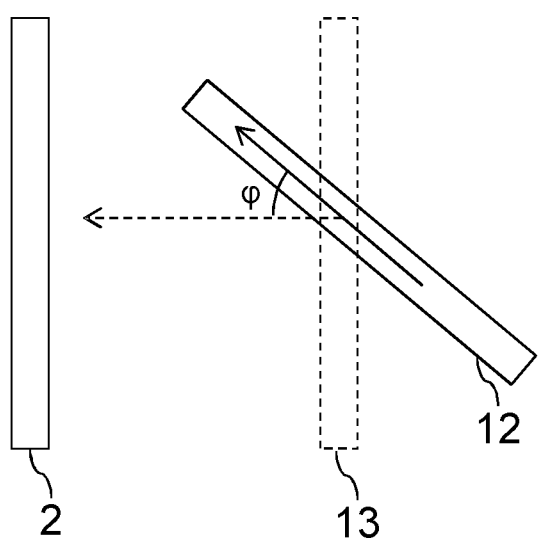
FIG. 6 is an annotated, simplified cross-section through a blood vessel and an ultrasound transducer.

FIG. 6 shows a portion of a major vessel from the blood vessel system 12, oriented at an angle $\varphi$ to the transducer 2. Suppose it has a cross-sectional area of a and that blood is moving along the portion in the direction of the arrow with velocity v. Then the volume of blood in the intersection of the sample volume 13' and the major blood vessel is $d*a/\cos(\varphi)$.

The corresponding Doppler shift is $f_d=2*v*\cos(\varphi)/\lambda$. The power density spectrum $P(f_d)$ is proportional to the blood volume.

Significantly, the following set of equations (1) demonstrates that the product $P(f_d)*f_d$ is independent of the angle $\varphi$:

$$P(f_d)*f_d = k*[d*a/\cos(\varphi)]*[2*v*\cos(\varphi)/\lambda] \quad (1)$$
$$= k*(2*d/\lambda)*(v*a)$$
$$= k*(2*d/\lambda)*q$$

Here k is a scaling constant which depends on the ultrasound attenuation, and q is the volume flow in the blood vessel. If several vessel intersect the sample volume, each of them will contribute to the power spectrum according to equation (1). The total volume flow through the sample volume 13' can then be found by integrating the equation (1) over all frequencies in the Doppler spectrum, as follows:

$$q = \frac{1}{k}*\frac{\lambda}{2*d}\int f \cdot P(f) \cdot df \quad (2)$$

To exclude the influence of thermal noise, which will be constant for all frequencies, the thermal noise can be estimated from the signal when the transmit power is turned off, and subtracted from the power spectrum before this integration.

Note that this equation (2) is valid even when the blood velocity varies over the vessel cross-section. This can be seen as follows: consider dividing the cross section into small subareas, where the velocity is constant, and calculating the sum by integration. Note also that the measured blood flow q is independent of the angle $\varphi$. This is important, since there is no way to measure the vessel angle, due to the absence of an imaging system. The ultrasound wavelength $\lambda$ and the sample-volume thickness are known, but the scaling constant k is not known: it depends on the scattering coefficient of blood, as well as attenuation of the ultrasound wave between the transducer and the blood vessel. If the method is used for monitoring with the transducer 2 in a fixed position relative to the patient 5, changes in instantaneous flow rate can be measured accurately. However, the method is sensitive to probe motion, and variation in acoustical contact with the skin line.

To meet this problem, the signal from the tissue surrounding the blood vessels (muscles, vessel walls etc.) can be used as a reference. Unlike blood, the signal from the surrounding tissue has no Doppler shift, since it is stationary. In practice, there may still be small vibrations or movements that give some Doppler shift, but this shift is smaller than from moving blood. It can be separated from the original signal with a low-pass filter. The signal from blood at speeds above a certain limit can be extracted by a high-pass filter. The signals from blood with low speed are therefore not included in the calculation of blood flow; this is not generally problematic because, due to their low speed, their contribution to the total flow will be marginal.

The power of the low-frequency signal, $P_{LF}$, and of the high-frequency signal will be affected equally by the attenuation, so the measured flow value can be made independent of attenuation by $$q \sim \frac{1}{P_{LF}} \int f \cdot P(f) \cdot df$$

Instead of the microcontroller 6 of display device 4 carrying out these integral calculations, in other embodiments, they may instead use an autocorrelation-based approach to estimate the power-weighted mean frequency, which can reduce the computational burden. Such an autocorrelation technique is described in "Abnormalities of left ventricular filling in patients with coronary artery disease: assessment by colour M-mode Doppler technique" by Stugaard M, Brodahl U, Torp H, Ihlen H (Eur Heart J. 1994 March; 15(3):318-27). In this case, a measure proportional to the blood volume flow q is then estimated by evaluating:

$$q \sim \frac{P_B}{P_{LF}} \arg(R_B)$$

Here $P_B$ and $R_B$ are the signal power and complex autocorrelation function with lag=1 sample.

Note that neither the integral approach nor the autocorrelation approach provides a calibrated values of flow rate (e.g., in ml/sec). However, temporal variations in blood flow over each heartbeat, or longer time sequences, can nevertheless be monitored correctly using these proportional measures.

These techniques can be applied to large blood vessels (typically 0.2 cm² to 1 cm²), provided that the cross-section is completely covered by the ultrasound beam. They can also be applied to a network of smaller blood vessels. In both cases a measurement is estimated that is relatively insensitive to adjustments of the position and angle of the ultrasound transducer 2, and may therefore be used by personnel without special training. They also enable the system 1 to be used to monitor blood flow, without substantial interference due to motion, to provide an automatic alarm function by unexpected changes in blood circulation.

Variations through the cardiac cycle, such as pulsatility, or other short-term responses in the blood flow to stimuli, can be measured. The system 1 can also be used for prolonged monitoring, as long as the transducer 2 stays in the same position. An example of this application, is the monitoring of blood flow in the brain of premature infants.

Premature babies have a higher occurrence of brain damage due to blood loss or unstable blood supply to the brain. The system 1 can be used to monitor blood flow to the brain, so that the treatment can be started quickly in the case of reduced blood supply. In contrast to using ultrasound colour Doppler imaging through fontanelle to inspect the blood flow through the fontanelle, which can only be performed sporadically, and requires an operator with extensive experience, the present blood flow monitoring system 1 uses a simplified, small and light ultrasonic Doppler transducer 2 which captures the blood flow of a relatively large area under fontanelle. It may have wireless connection to a tablet or PC. The location and angle of the transducer 2 are not critical, meaning that the system 1 can be operated by a healthcare professional without specialist training in ultrasound. The system 1 is inexpensive to manufacture, and enables new opportunities for continuous monitoring of preterm infants in the first critical stage of life.

A single measurement of instantaneous blood flow can be obtained over a period of 5 milliseconds to 10 milliseconds. Repeated measurements from partially-overlapping periods enables the system 1 to generate a blood flow curve with sufficient time resolution for waveform analysis. From this curve, the system 1 can then calculate a time average (e.g., over 1-10 heartbeats). Pulsative/resistive index, which is related to the elastic property of the vessel, can be calculated from the waveform.

By taking repeated measurements with different peripheral resistance, the system 1 can use the waveform, combined with a Wind Kessel-model, to estimate a parameter proportional to volume compliance. This can be calculated based on volume flow curves.

It will be appreciated by those skilled in the art that the invention has been illustrated by describing one or more specific embodiments thereof, but is not limited to these embodiments; many variations and modifications are possible, within the scope of the accompanying claims.

The invention claimed is:

1. A system for monitoring blood flow in a patient, the system comprising:
    a first unit comprising a single-element ultrasound transducer and a fastener for fastening the first unit to the patient;
    a controller subsystem; and
    a monitoring subsystem,
    wherein the controller subsystem is configured to:
        control the single-element ultrasound transducer to transmit plane-wave pulses into the patient in a propagation direction;
        sample reflections of the plane-wave pulses, received at the single-element ultrasound transducer, from a region within the patient, to generate pulse-Doppler response signals; and
        process the pulse-Doppler response signals to estimate a series of values, over time, of a measure proportional, but not equal, to a total blood volume flow passing through the region, and
    wherein the monitoring subsystem is configured to monitor the series of values over time and to generate a signal if a set of one or more of the values satisfies a predetermined criterion.

2. The system of claim 1, wherein there is no acoustic lens in front of the ultrasound transducer.

3. The system of claim 1, wherein the ultrasound transducer is arranged to transmit an unfocussed beam having a constant cross-section in the propagation direction.

4. The system of claim 1, wherein the controller subsystem is configured to use range gating to control an extent of the region in the propagation direction.

5. The system of claim 1, wherein the fastener comprises a strap.

6. The system of claim 1, wherein the controller subsystem is configured to estimate a power spectrum relating to thermal noise and to subtract the power spectrum of the thermal noise from a power spectrum generated from the sampled reflections.

7. The system of claim 1, wherein the controller subsystem is configured to store a value representing a power-weighted mean frequency of at least part of one of the pulse-Doppler response signals in a memory of the system.

8. The system of claim 7, wherein the controller subsystem is configured to calculate the value representing the power-weighted mean frequency by integrating, over a set of frequencies, power multiplied by frequency for the pulse-Doppler response signal, or by using an autocorrelation function of a complex envelope signal of part or all of the pulse-Doppler response signal.

9. The system of claim 1, wherein the controller subsystem is configured to determine each value of the measure from a respective power-weighted mean frequency of at least part of one of the pulse-Doppler response signals.

10. The system of claim 1, wherein the measure proportional to the total blood volume flow passing through the region is equal to the total blood volume flow passing through the region multiplied by a coefficient of proportionality, wherein said coefficient of proportionality depends on a scattering co-efficient of blood in the region and on ultrasound attenuation between the ultrasound transducer and the region.

11. The system of claim 1, wherein the controller subsystem is configured to compensate for attenuation between the transducer and the region by scaling the measure proportional to the total blood volume flow through the region according to an estimate of said attenuation.

12. The system of claim 1, wherein the controller subsystem is configured to calculate a blood flow curve from said series of values, over time.

13. The system of claim 1, wherein the controller subsystem is configured to sample reflections of the plane-wave pulses from each of a plurality of regions within the patient, and to determine respective series of values of the measure proportional to the total blood flow through the respective region for each of the plurality of regions.

14. The system of claim 1, wherein the controller subsystem comprises a second unit separate from the first unit; and wherein the first unit is configured to send data representing the pulse-Doppler response signals to the second unit over a wired or wireless link.

15. A method of monitoring blood flow in a patient, the method comprising:
fastening a unit comprising a single-element ultrasound transducer to the patient;
transmitting plane-wave ultrasound pulses into the patient from the single-element ultrasound transducer in a propagation direction;
sampling reflections of the plane-wave pulses from a region within the patient, received at the single-element ultrasound transducer, to generate pulse-Doppler response signals;
processing the pulse-Doppler response signals to estimate a series of values, over time, of a measure proportional, but not equal, to a total blood volume flow passing through the region;
determining whether the series of values meets a predetermined alert criterion; and
signalling an alert if the series of values meets the predetermined criterion.

16. The method of claim 15, comprising calculating a power-weighted mean frequency of at least part of one of the pulse-Doppler response signals by integrating, over a set of frequencies, power multiplied by frequency for the pulse-Doppler response signals, or by using an autocorrelation function of a complex envelope signal of part or all of the pulse-Doppler response signal.

17. The method of claim 15, comprising compensating for attenuation between the transducer and the region by scaling the measure proportional to the total blood volume flow through the region according to an estimate of said attenuation.

18. The method of claim 15, wherein each value of the series of values relates to blood flow through the region at a respective point in time, and wherein the points in time span an interval longer than a minute.

19. The method of claim 15, wherein each value of the series of values relates to blood flow through the region at a respective point in time, and wherein the points in time span an interval longer than an hour.

20. The method of claim 15, wherein the region contains a plurality of blood vessels and wherein the measure is proportional, but not equal, to the total blood volume flow passing through the plurality of blood vessels in the region.

* * * * *